United States Patent
Coletti

Patent Number: 5,863,285
Date of Patent: Jan. 26, 1999

[54] BALLOON CATHETER WITH RADIOACTIVE MEANS

[75] Inventor: Paul A. Coletti, Belle Mead, N.J.

[73] Assignee: Cordis Corporation, Miami, Fla.

[21] Appl. No.: 790,778

[22] Filed: Jan. 30, 1997

[51] Int. Cl.⁶ .................................................. A61N 5/00
[52] U.S. Cl. ................................................................ 600/3
[58] Field of Search ............................................ 600/1–8

[56] References Cited

U.S. PATENT DOCUMENTS

| | | | |
|---|---|---|---|
| 4,762,130 | 8/1988 | Fogarty et al. | |
| 5,059,166 | 10/1991 | Fischell et al. | 600/3 |
| 5,084,002 | 1/1992 | Liprie | 600/7 |
| 5,141,487 | 8/1992 | Liprie | 600/7 |
| 5,199,939 | 4/1993 | Dake et al. | 600/3 |
| 5,282,781 | 2/1994 | Liprie | 600/3 |
| 5,302,168 | 4/1994 | Hess | 600/3 |
| 5,411,466 | 5/1995 | Hess | 600/3 |
| 5,503,613 | 4/1996 | Weinberger | 600/3 |
| 5,503,614 | 4/1996 | Liprie | 600/7 |
| 5,540,659 | 7/1996 | Teirstein | 604/104 |
| 5,643,171 | 7/1997 | Bradshaw et al. | 600/1 |
| 5,662,580 | 9/1997 | Bradshaw et al. | 600/3 |
| 5,722,984 | 3/1998 | Fischell et al. | 600/3 X |
| 5,725,572 | 3/1998 | Lam et al. | 600/3 X |

FOREIGN PATENT DOCUMENTS

| | | |
|---|---|---|
| 0 593 136 A1 | 4/1994 | European Pat. Off. . |
| 317655 | 9/1928 | United Kingdom ........................ 600/1 |
| WO 94/25106 | 11/1994 | WIPO . |

*Primary Examiner*—John P. Lacyk
*Assistant Examiner*—Samuel Gilbert

[57] ABSTRACT

The invention relates to a catheter comprising a tube-like basic body with a distal and a proximal end, a balloon device arranged close to the distal end comprising at least one balloon member and carrying a radioactive conductor arranged in a pattern. The pattern comprises a number of coil shapes, each having a coil axis, and whereby the coil axes of the coil shapes can extend in different directions.

16 Claims, 2 Drawing Sheets

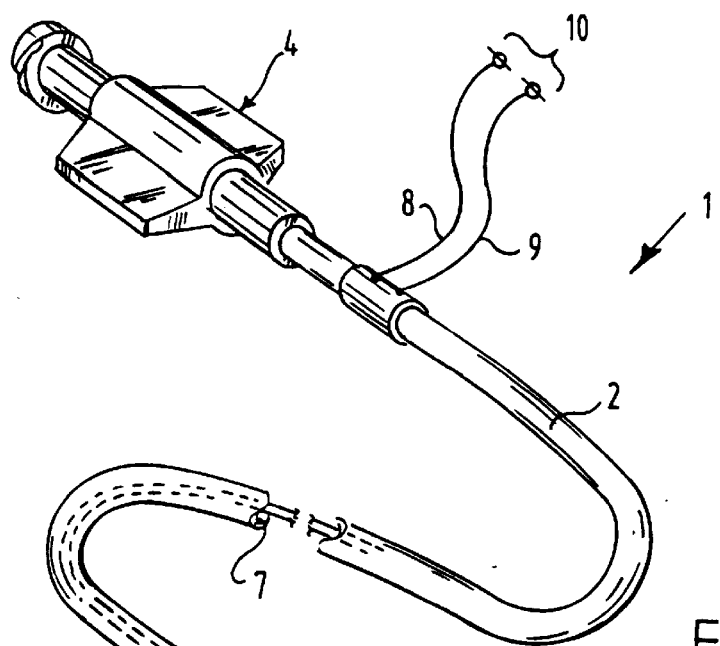
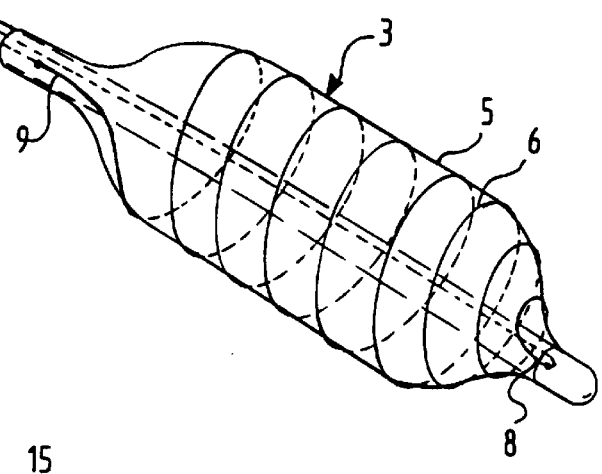
FIG.1
FIG.2

BALLOON CATHETER WITH RADIOACTIVE MEANS

BACKGROUND OF THE INVENTION

This invention relates to a catheter which is particularly intended for use during internal therapy of a patient under radiation to reduce stenosis or restenosis in a lumen.

The radioactive conductor integral with and carried by the balloon device is introduced into a patient together with the balloon device. When doing so any balloon members of the balloon device are deflated, so that this device has a small diameter.

When the balloon device has been maneuvered into the target position inside the body of the patient, the balloon member may be inflated in order to unfold the radioactive conductor which has been arranged in a predetermined pattern. There is an interaction between the conductor and the lumen, which provides a number of diagnostic possibilities.

A suitable electric current may for instance be simultaneously fed to the conductor, as a result of which a magnetic field is created affecting the field of the MRI device, producing visible effects on the MRI screen. The conductor may also be entirely passive and result in radioactive energy being provided to the lumen. The device may also be used by inducing an electric current in the conductor, of which the various properties can be measured.

The invention will be explained in greater detail in the following description with reference to the attached figures.

DESCRIPTION OF THE DRAWINGS

FIG. 1 shows a partly broken away and partly schematic perspective view of a balloon catheter according to the invention;

FIG. 2 illustrates a distal end of a balloon catheter according to another embodiment;

DESCRIPTION OF THE INVENTION

Figure 3:
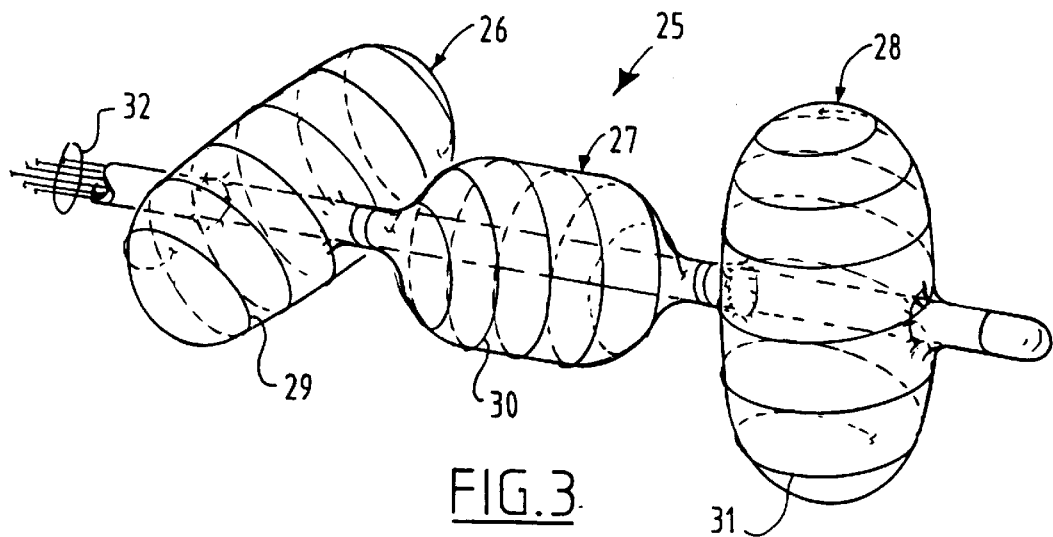
FIG. 3 shows a third embodiment of the balloon device of the catheter according to the invention.

The catheter 1 according to the invention illustrated in FIG. 1 comprises a tube-like basic body with a balloon device 3 at a distal end, which comprises in this embodiment 1 a balloon member 5. A connecting member 4 has been arranged at the opposite proximal end, through which a lumen 7 in the tube-like body 2 is accessible and through which for instance a medium under pressure can be supplied to the balloon member 5, in order to expand the balloon member 5 from the deflated introduction state into the inflated state use illustrated.

As can be seen in the figure the balloon member 5 carries a radioactive conductor 6 arranged in a pattern, whereby the pattern is in the case of this embodiment a coil shaped, although by no means is a coil the only preferred embodiment. Both ends of the coil shape are connected to connecting lines 8, 9 which have been led through the wall of the basic body 2 to the proximal end of the catheter 2. In another embodiment the connecting lines can run through a separate lumen. Close to the proximal end the conductors 8, 9 have been led outside and end in a connection 10.

A suitable radioactive source may be connected to the connection 10, which source can supply a direct current or alternating current with any waveform along with a radioactive after load. Or, prior to insertion, conductor 6 can be molded within balloon member 5, already in a radioactive stent. As a result a suitable radioactive field is generated around the balloon member 5 by the conductor 6 arranged in a coil shape. The consequent effect on the field created by the catheter provides radiation on the area inside the lumen of the body of the patient of where the balloon device 3 is situated, thereby allowing radiation therapy to reduce restenosis.

With another mode of use the coil 6 is used as a receiving device in the surrounding electromagnetic field. With this receiving device the intensity of the field at that site can be determined, which once again may provide information on the nature of the tissue of the patient surrounding the balloon device 3.

With the balloon device 3 of FIG. 1 the coil shape 6 arranged on it has a coil axis which is substantially coaxial with the longitudinal axis of the basic body 2.

It may also be desirable however to have a coil with a coil axis at a different angle at one's disposal. This has been realized in the embodiment of FIG. 2. The balloon device 15 of FIG. 2 comprises a balloon member 16 and a balloon member 18 arranged inside it. The outer balloon member 16 carries a radioactive conductor 17 arranged in a coil shape, of which the coil axis is placed at right angles to the longitudinal direction of the basic body of the catheter.

The inner balloon member 18 carries a radioactive conductor 19, once again arranged in a coil shape, of which the coil axis is coaxial with the longitudinal axis of the basic body. Thus two coil shapes are provided with coil axes positioned at right angles to one another.

Each conductor 17, 19 is again connected to connecting lines 20, 21 which have been led to the proximal end.

Supplying medium under pressure in order to expand the balloon members 16, 18 takes place via lumens in the basic body, which have not been illustrated in detail.

The basic body furthermore comprises a lumen 22 which extends through the entire basic body and is open at the extreme distal end. A guide wire may be advanced through this lumen 22, in order to guide the distal end of the catheter to the target position inside the body of a patient.

Arranged possibility to realize coil shapes with coil axes positioned at angles to each other has been illustrated in FIG. 3. In this case the balloon device 25 illustrated comprises three balloon members 26, 27, 28, which have been arranged one behind the other to be basic body. Each of the balloon members 26, 27, 28 has a longitudinal shape and carries an radioactive conductor 29, 30, 31 respectively with a coil axis which runs substantially parallel to the longitudinal axis of the balloon member concerned. By means of the illustrated arrangement of the balloons 26–28 three coils 29, 30, 31 are formed, with three axes at right angles to one another, so that the intensity of the radioactivity can be determined or influenced in three directions at rights angles to one another. The connecting lines 22 connected to the electrical conductors on the balloon members have once again been led via the body to its proximal end of the catheter.

In another embodiment the balloon members can have the more usual sphere shape.

The conductors may be arranged to the balloon members in different manners. Suitable is arranging the conductor by means of a deposition technique, such as for instance vacuum deposition. The conductor will in that case be very flexible and can adapt to the deformations of the balloon member concerned, without an interruption in radioactivity occurring in the conductor and without sacrificing flexibility.

One can also choose for a wire-like conductor however, which is glued to a balloon member, melted onto it or is included in a double wall.

Figure 4:
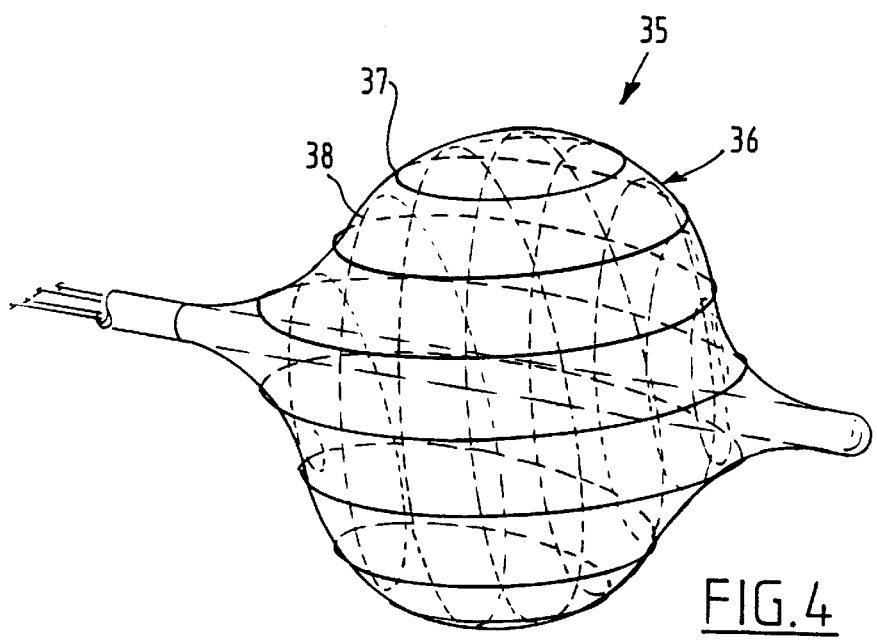
FIG. 4 shows a fourth embodiment.

With the embodiment illustrated in FIG. 4, the balloon device 35 comprises one balloon member 36 with two radioactive conductors 37, 38. The conductor 37 has been arranged just in the outer surface of the balloon member 36 and the conductor 38 has been arranged nearer to the inner surface of the balloon member 36. The conductors can also be arranged on one and the same surface, preferably the outer one. As can be seen in the figure, the conductors 37, 38 have once again been arranged in coil shapes, whereby the coil axes of these coil shapes are in this case positioned at right angles to each other.

Although in the embodiments shown here each time coil shapes with a cylindrical or spherical basic shape have been shown for the sake of clarity, the conductor may be arranged on or within the balloon members in any desired pattern. The shape employed also depends on the expanded shape which has been chosen for the balloon member. In addition to the coil shapes illustrated, also spiral shapes, zigzag shapes, et cetera are possible. By choosing a suitable balloon member, also saddle shaped coils can be obtained in the expanded state of the balloons concerned.

With the embodiment of FIG. 2 it may for instance be possible that the inner balloon member 18 can be expanded independently of the outer balloon member 16. As a result treatment may be carried out whilst only the outer balloon member 16 is expanded and the inner balloon member 18 still is deflated. Also in the case of an embodiment as illustrated in FIG. 3, the balloon members 26–28 may be made in such a way that they can be expanded independently of one another.

Because the conductor is radioactive, there is the possibility of providing restenosis therapy to the lumen. The device is:

1) Centered on the lumen of the body by being located in the catheter wall;
2) Radioactive to prevents stenosis;
3) Uses existing devices and technology so that it is easy and now relatively inexpensive to manufacture.

The connecting lines of the conductors on the balloon members to the proximal end of the catheter may be embodied in many different ways. For each conductor on a balloon member a separate pair of connecting lines running to the proximal end may be employed in the manner illustrated but, in the case of these conductors being electrical connectors as well, a multiplexer may for instance be used as well. Electronic circuits such as preamplifiers and tuning and adapting electronics may be received in said connecting lines. All these and similar embodiments are considered to fall within the scope of the attached claims.

I claim:

1. A balloon catheter used for inflation of a lumen, said balloon comprising a shaft having proximal and distal ends and a lumen therethrough, and said shaft distal end attached to an inflatable balloon, said balloon having a lumen in communication with the lumen of said shaft, and said balloon having a reinforcing metallic layer molded therein; and further comprising said metallic layer being made of a radioactive material, so that upon inflation of said balloon, the radioactive metallic layer comes into the proximity of the walls of a body lumen;
wherein said radioactive metallic layer is patterned in a coil shape; and
wherein the pattern comprises a number of coil shapes, each comprising a coil axis, and wherein the coil axes of the coil shapes extend in different directions.

2. Catheter as claimed in claim 1, comprising three coil shapes, wherein the coil axes are positioned substantially at right angles to one another.

3. Catheter as claimed in claim 1 wherein each said coil shape is carried by a separate balloon member.

4. Catheter as claimed in claim 1 wherein connecting lines have been connected to ends of the radioactive metallic layer, which extend to the proximal end through the walls of said catheter.

5. Catheter as claimed in claim 4, comprising three coil shapes, wherein the coil axes are positioned substantially at right angles to one another.

6. Catheter as claimed in claim 4 wherein each said coil shape is carried by a separate balloon member.

7. Catheter as claimed in claim 4 wherein the radioactive metallic layer has been fixed to the material of the balloon member by means of a low extrusion process.

8. Catheter as claimed in claim 4 wherein the balloon member is made of a thermoplastic material and the radioactive metallic layer is encased in the material from which the balloon member is made.

9. Catheter as claimed in claim 1 wherein the radioactive metallic layer has been fixed to the material of the balloon member by means of a low extrusion process.

10. Catheter as claimed in claim 1 wherein the balloon member is made of a thermoplastic material and the radioactive metallic layer is encased in the material from which the balloon member is made.

11. A balloon catheter used for inflation of a lumen, said balloon comprising a shaft having proximal and distal ends and a lumen therethrough, and said shaft distal end attached to an inflatable balloon, said balloon having a lumen in communication with the lumen of said shaft, and said balloon having a reinforcing metallic layer molded therein; and further comprising said metallic layer being made of a radioactive material, so that upon inflation of said balloon, the radioactive metallic layer comes into the proximity of the walls of a body lumen;
wherein said radioactive metallic layer is patterned in a coil shape;
wherein the pattern comprises a number of coil shapes, each comprising a coil axis, and wherein the coil axes of the coil shapes extend in different directions; and
wherein connecting lines have been connected to ends of the radioactive metallic layer, which extend to the proximal end through the walls of said catheter.

12. A balloon catheter used for inflation of a lumen, said balloon comprising a shaft having proximal and distal ends and a lumen therethrough, and said shaft distal end attached to an inflatable balloon, said balloon having a lumen in communication with the lumen of said shaft, and said balloon having a reinforcing metallic layer molded therein; and further
comprising said metallic layer being made of a radioactive material, so that upon inflation of said balloon, the radioactive metallic layer comes into the proximity of the walls of a body lumen;
wherein said radioactive metallic layer is patterned in a coil shape;
wherein the pattern comprises a number of coil shapes, each comprising a coil axis, and wherein the coil axes of the coil shapes extend in different directions; and
wherein each said coil shape is carried by a separate balloon member.

13. Catheter as claimed in claim 12, comprising three coil shapes, wherein the coil axes are positioned substantially at right angles to one another.

14. Catheter as claimed in claim 12 wherein connecting lines have been connected to ends of the radioactive metallic layer, which extend to the proximal end through the walls of said catheter.

15. Catheter as claimed in claim 12 wherein the radioactive metallic layer has been fixed to the material of the balloon member by means of a low extrusion process.

16. Catheter as claimed in claim 12 wherein the balloon member is made of a thermoplastic material and the radioactive metallic layer is encased in the material from which the balloon member is made.

* * * * *